United States Patent [19]
Kontos

[11] Patent Number: 5,980,539
[45] Date of Patent: Nov. 9, 1999

[54] DEVICE AND METHOD FOR SUTURING BLOOD VESSELS AND THE LIKE

[75] Inventor: Stavros Kontos, Woodcliff Lake, N.J.

[73] Assignee: X-Site L.L.C., N.J.

[21] Appl. No.: 09/073,462

[22] Filed: May 6, 1998

[51] Int. Cl.$^6$ .................................................. A61B 17/04
[52] U.S. Cl. ........................... 606/148; 606/144; 606/233
[58] Field of Search ..................................... 606/148–170, 606/139, 140, 141–147, 205, 207, 213, 232, 233; 604/272

[56] References Cited

U.S. PATENT DOCUMENTS

| | | |
|---|---|---|
| 4,107,953 | 8/1978 | Casillo . |
| 4,757,827 | 7/1988 | Buchbinder et al. . |
| 4,799,495 | 1/1989 | Hawkins et al. . |
| 4,890,612 | 1/1990 | Kensey . |
| 5,108,421 | 4/1992 | Fowler . |
| 5,304,184 | 4/1994 | Hathaway et al. . |
| 5,312,360 | 5/1994 | Behl . |
| 5,324,306 | 6/1994 | Makower . |
| 5,336,229 | 8/1994 | Noda . |
| 5,336,231 | 8/1994 | Adair . |
| 5,383,896 | 1/1995 | Gershony et al. . |
| 5,391,183 | 2/1995 | Janzen et al. . |
| 5,417,699 | 5/1995 | Klein et al. . |
| 5,431,666 | 7/1995 | Sauer et al. . |
| 5,437,631 | 8/1995 | Janzen . |
| 5,447,502 | 9/1995 | Haaga . |
| 5,474,543 | 12/1995 | McKay . |
| 5,527,322 | 6/1996 | Klein . |
| 5,578,044 | 11/1996 | Gordon et al. . |
| 5,613,974 | 3/1997 | Andreas . |
| 5,676,689 | 10/1997 | Kensey . |
| 5,728,133 | 3/1998 | Kontos . |
| 5,855,585 | 1/1999 | Kontos . |

FOREIGN PATENT DOCUMENTS

| | | |
|---|---|---|
| 0 637 431 | 2/1995 | European Pat. Off. . |
| 95/13021 | 5/1995 | WIPO . |

*Primary Examiner*—Michael Buiz
*Assistant Examiner*—Lien Ngo
*Attorney, Agent, or Firm*—Kenyon & Kenyon

[57] ABSTRACT

A device for sealing a hole in an anatomical structure comprises an elongated member formed with a proximal portion extending along a first axis and a distal portion extending along a second axis, wherein the second axis is different from the first axis and wherein a needle retention channel extends within the distal portion to a distal opening formed in the proximal end of the distal portion. A central portion connects the proximal and distal portions. In use, the device is guided into the hole in the anatomical wall and positioned in a first orientation so that the distal opening faces a first desired location on the inner wall. Thereafter, a first needle is withdrawn from the needle retention channel by drawing proximally a suture coupled to the first needle so that the first needle passes through the first desired location out of the body. The elongated member is then rotated within the hole to a second orientation so that the distal opening faces a second desired location on the inner wall. The second needle is then withdrawn from the first needle retention channel by drawing a second portion of the suture proximally so that the second needle passes through the second desired location out of the body and the ends of the length of are tied together to seal the hole.

11 Claims, 16 Drawing Sheets

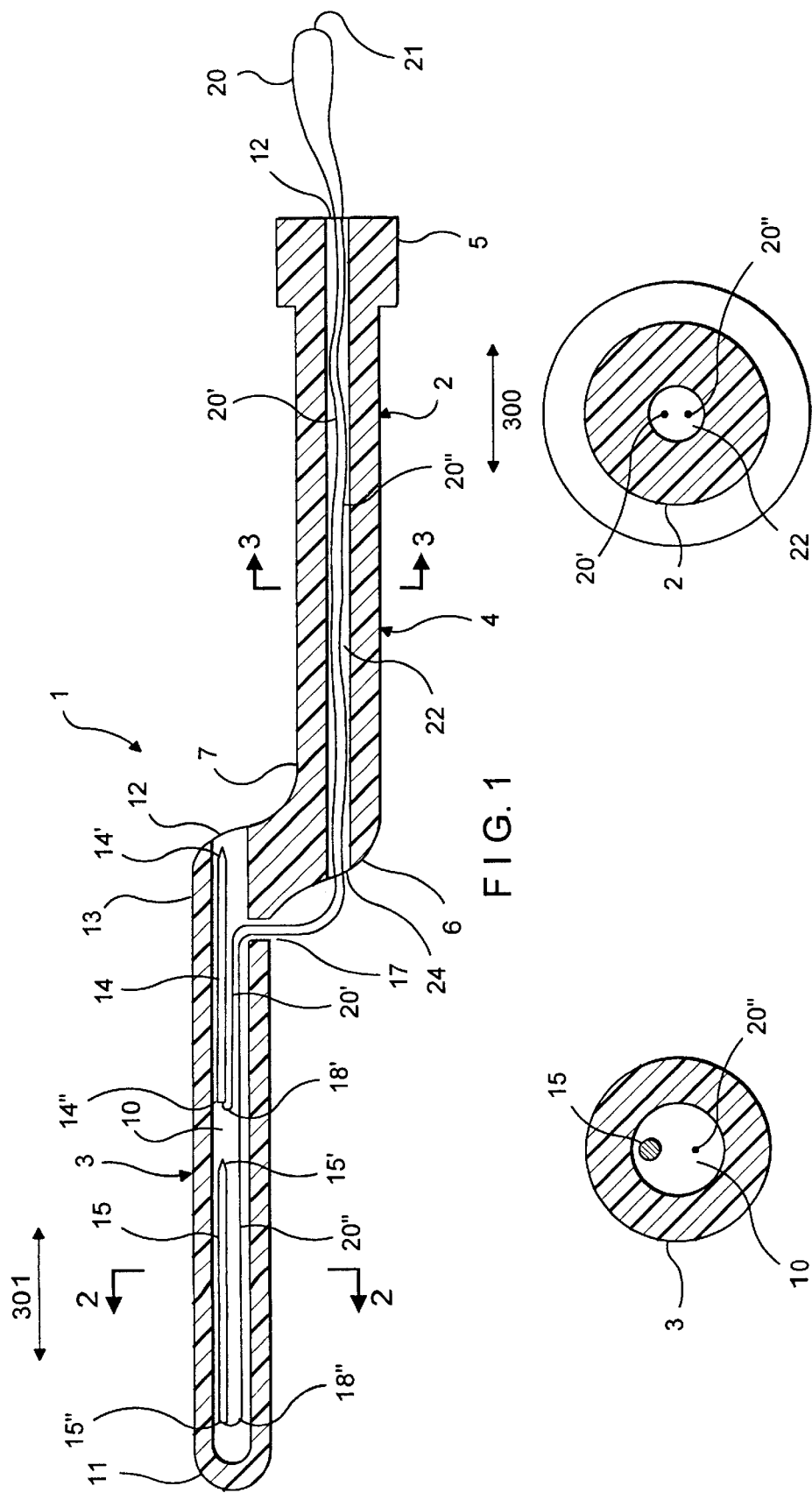

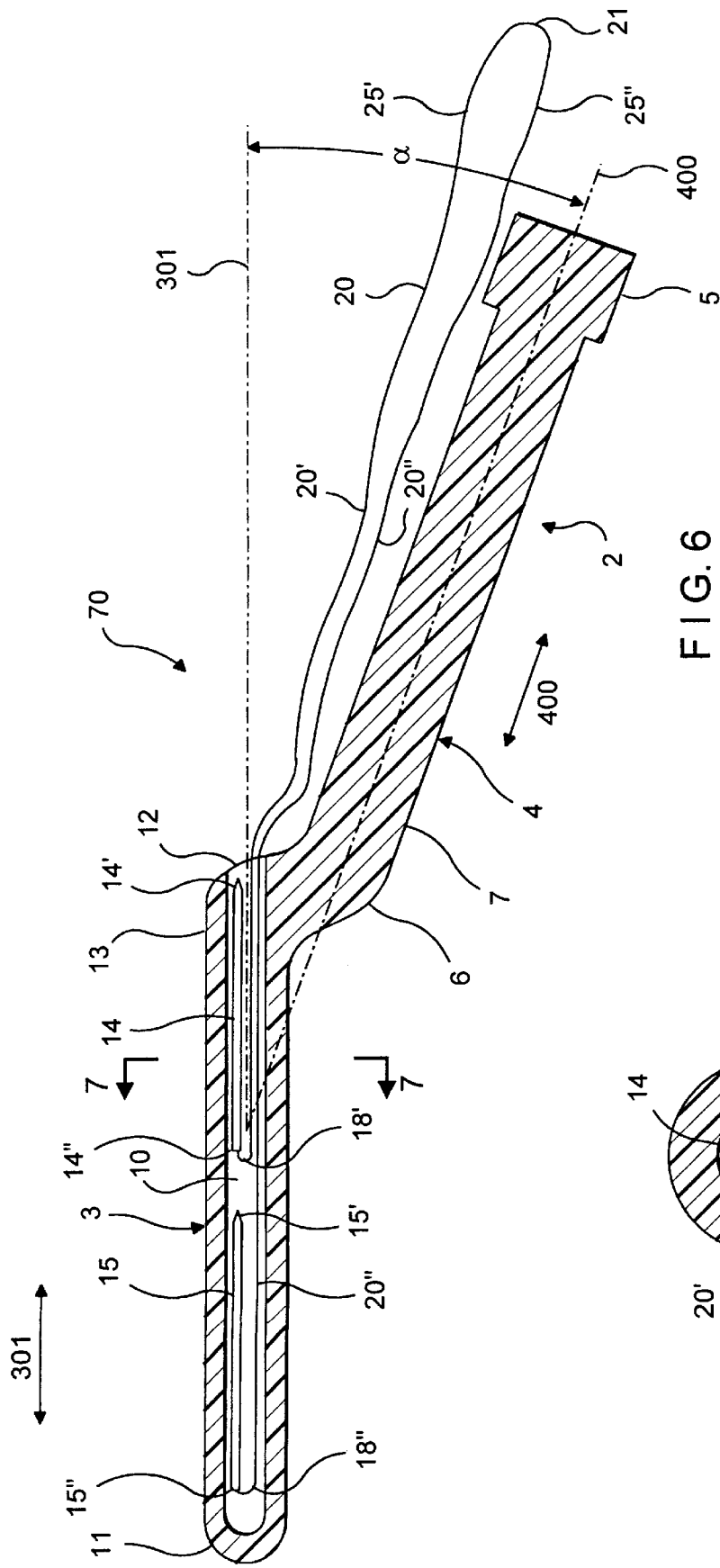
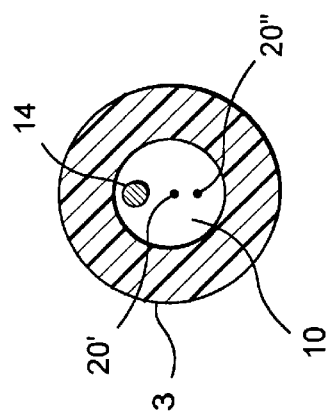
FIG. 6
FIG. 7

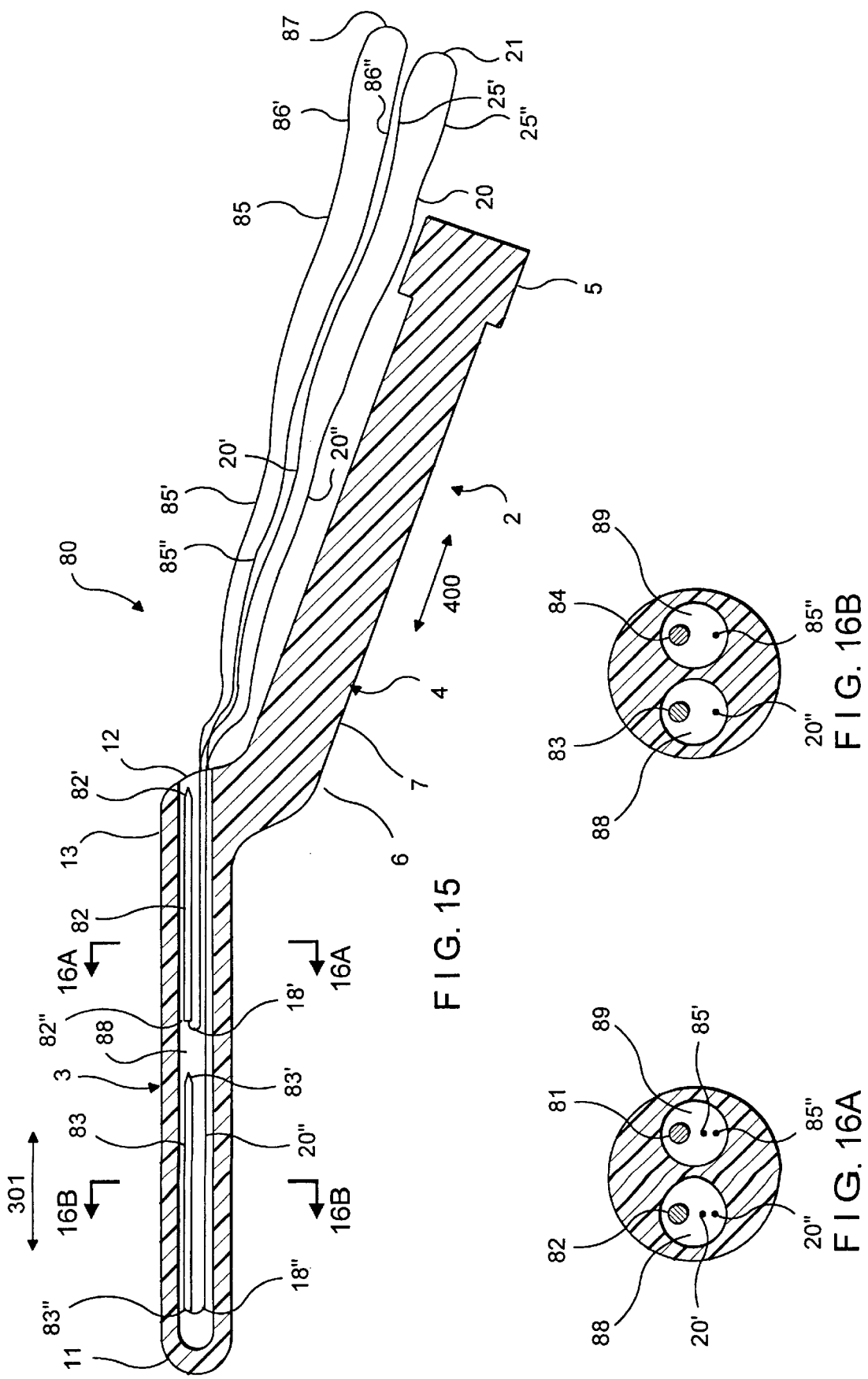

DEVICE AND METHOD FOR SUTURING BLOOD VESSELS AND THE LIKE

FIELD OF THE INVENTION

The present invention relates generally to surgical instruments, and more specifically to devices for the suturing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument, i.e., a catheter, into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the sides of the opening in the wall of the blood vessel must be sealed to prevent bleeding while facilitating healing of the wound. At present, this sealing is commonly accomplished by application of direct pressure over the puncture site by a physician or other trained medical professional. Due to the dangers of thrombosis, the substantial reduction of blood flow through the blood vessel due to the application of pressure is undesirable and potentially dangerous to the patient. In addition, the procedure is extremely time consuming; often requiring that pressure be applied for forty-five minutes or more to achieve acceptable sealing.

Other sealing techniques include the application of a biogenic sealing material over the opening to seal the wound. However, proper placement of the sealing material is difficult to achieve and, the plug of sealing material left inside the blood vessel may result in serious health risks to the patient.

As a result, devices have been developed which are inserted through the puncture in order to suture openings created in blood vessels. However, these devices suffer from various drawbacks.

For example, U.S. Pat. No. 5,417,699 to Klein et al. describes a device wherein two needles coupled to a distal end of an insertion shaft are surrounded by an outer sheath during insertion into an internal structure. Once inside the internal structure, the outer sheath is withdrawn and bowed sections of the needles, which had been constrained within the outer sheath against an outward spring bias, deploy away from the insertion shaft. The insertion shaft is then withdrawn drawing the needles through the walls of the internal structure. The arcuate shape of the needles is intended to bring the needles back along a curved path toward the insertion shaft so that the free ends of the needles may be captured on the shaft and the device withdrawn from the body. Thereafter, the distal ends of the needles must be detached from the insertion shaft so that a length of suture extending between distal ends of the two needles may be drawn through the walls of the internal structure to seal the opening.

However, the curved shape of the proximal ends of the needles of this device requires an insertion sheath of increased diameter. Thus, after withdrawal of a treatment catheter from an opening formed in an internal structure, insertion of the increased diameter outer sheath of the device of Klein et al. actually expands the opening in the wall of the internal structure. In addition, the device of Klein et al. employs several slidably mounted concentric shafts and mechanisms for the deployment and capture of the needles which make the device costly to manufacture and cumbersome to operate.

SUMMARY OF THE INVENTION

The present invention is directed to a device for sealing an opening in an anatomical structure within a living body. The device includes a tube having a proximal part, which extends along a first axis. The device also includes a distal part extending along a second axis that is different from the first axis, and a central part coupling the proximal part to the distal part. At least one needle retention channel is formed within the distal part for holding needles. The needle retention channel extends to a distal part opening formed in the proximal end of the distal part. In operation, the device is positioned in a first desired orientation so that the distal part opening faces a first interior portion of the wall of the anatomical structure. Then, a first needle of the plurality of needles coupled to a first end of a length of suture is projected through the needle retention channel, so that a first sharp forward end of the first needle passes through the anatomical structure wall at a first location. The needle is then extracted. The device is then rotated within the opening to a second desired orientation so that the distal part opening faces a second interior portion of the wall. In such orientation, a second needle coupled to a second end of the length of suture is projected through the needle retention channel so that a sharp forward end of the second needle passes through the anatomical structure at a second location. Finally, the first and second ends of the length of suture are coupled to seal the anatomical structure opening.

Another embodiment of the device and method according to the present invention includes two needle retention channels. Each of these channels situates at least a pair of needles. A first length of suture is coupled between the first pair of needles, and a second length of suture is coupled between the second pair of needles. When the device is positioned in a first orientation, a user pulls on a portion of the first length of suture to draw a first needle of the first pair of needles from the first needle retention channel so that this needle exits the blood vessel at a first location. The user then pulls on a portion of the second length of suture to draw a first needle of the second pair of needles from the second needle retention channel so that this needle exits the blood vessel at a second location, and these needles are extracted. The device is then rotated within the opening to a second desired orientation. In such orientation, a second needle of the first pair of needles is projected through the needle retention channel, so that a sharp forward end of the second needle passes through the anatomical structure at a third location. Similar procedure is performed for the second needle of the second pair of needles so that the second needle of the second pair of needles exits the blood vessel at a fourth location. Finally, the ends of the first and second lengths of suture are coupled to seal the anatomical structure opening.

BRIEF DESCRIPTION OF THE DRAWINGS

FIG. 1 shows a cross-sectional side view of a surgical suturing device according to a first embodiment of the present invention.

FIG. 2 shows a cross-section of the device according to the first embodiment of the present invention taken along line 2—2 of FIG. 1.

FIG. 3 shows a cross-section of the device according to the first embodiment of the present invention taken along line 3—3 of FIG. 1.

FIG. 6 shows a cross-sectional side view of a surgical suturing device according to a fourth embodiment of the present invention.

FIG. 7 shows a cross-section of the device according to the fourth embodiment of the present invention taken along line 7—7 of FIG. 6.

FIG. 15 shows a cross-sectional side view of a surgical suturing device according to a fifth embodiment of the present invention.

FIG. 16A shows a cross-section of the device according to the fifth embodiment of the present invention taken along line 16A—16A of FIG. 15.

FIG. 16B shows a cross-section of the device according to the fifth embodiment of the present invention taken along line 16B—16B of FIG. 15.

DETAILED DESCRIPTION

Figure 4:
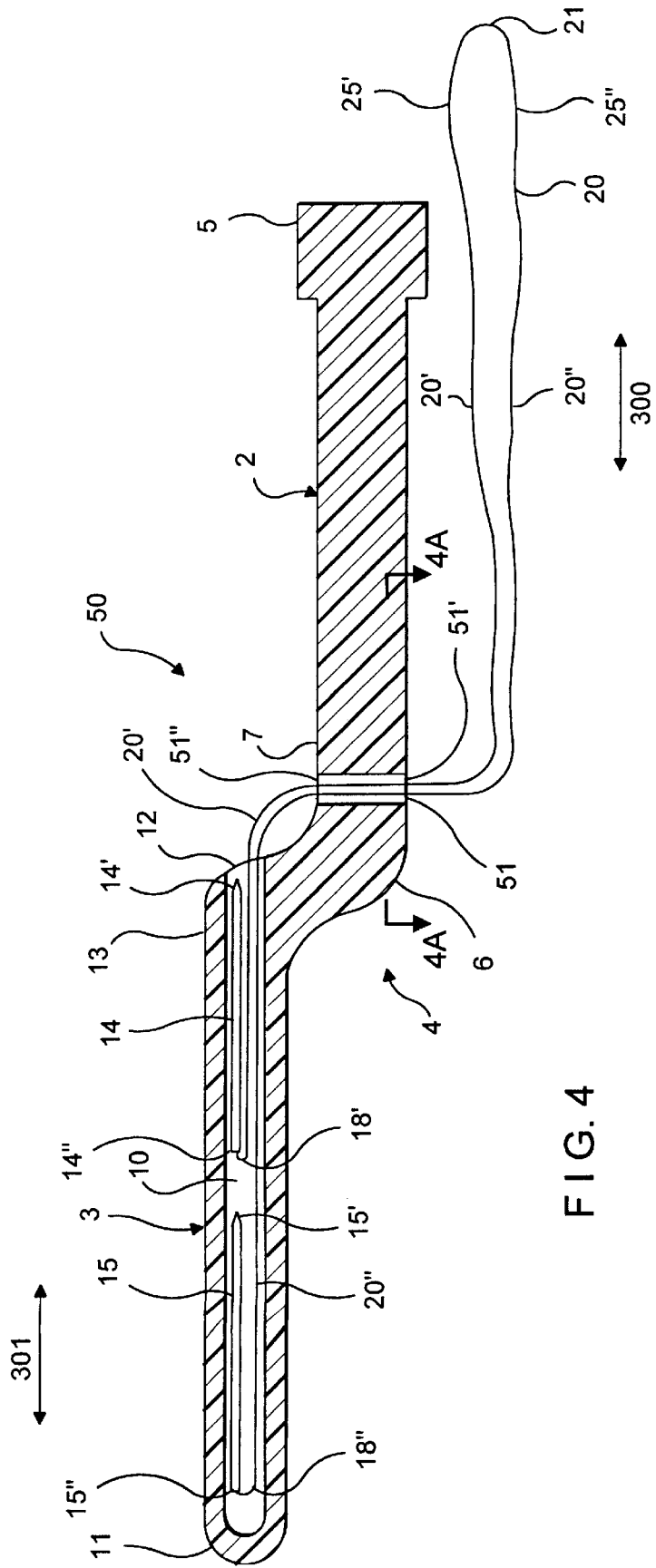
FIG. 4 shows a cross-sectional side view of a surgical suturing device according to a second embodiment of the present invention.

FIG. 1 shows a device 1 according to a first embodiment of the present invention for suturing punctures in blood vessels, internal organs and the like. The device 1 includes a flexible tube 4 which may preferably have a circular or elliptical cross-section. The flexible tube 4 includes a proximal part 2 extending along a first axis 300 and a distal part 3 extending along a second axis 301 substantially parallel to, and separated by a predetermined distance from, the first axis 300. The flexible tube 4 also includes a connecting part 6 which is situated between the proximal part 2 and the distal part 3. The proximal part 2 extends from a proximal end 5 to a distal end 7 which is coupled to a proximal end of the connecting part 6. The cross-section of the connecting part 6 may also be substantially circular or elliptical with a cross-sectional area substantially equal to a cross-sectional area of the distal part 3. Of course, the cross-sectional area of the proximal part 2 may also be substantially equal to that of the distal part 3. The flexible tube 4 is preferably constructed of a thermoplastic material such as polyurethane, polyethylene, or the like, and may consist of separate extruded or molded parts coupled together. It may be more economical to extrude those parts including one or two lumens (as described below), while other portions, i.e., connecting part 6 of the flexible tube 4, may be more economically molded. The length and diameter of the flexible tube 4 may be pre-selected to comply with the requirements of a particular situation. The length may preferably be between 4 cm and 20 cm, while the diameter may preferably be varied between 2.0 mm and 10.0 mm. Flexible tubes of other lengths may also be used as the situation demands. Other dimensions of the flexible tube 4 can also be conceivable. However, those skilled in the art will understand that the length of the device can be selected to correspond to the location which needs to be accessed and the diameter may be selected to correspond to the size of the vessel or structure into which the device is to be inserted.

The distal part 3 includes an interior needle lumen 10 which extends along the second axis 301 from a distal end 11 of the distal part 3 to a needle opening 12 formed in a proximal end 13 of the distal portion 3. As seen in FIG. 2, the needle lumen 10, which may preferably be substantially circular in cross-section, is sized and shaped to receive therein a first needle 14, a second needle 15 and a two end portions of a length of suture 20. The first needle 14 is preferably oriented with a pointed proximal end 14' thereof extending to a position adjacent to the proximal end 13 of the distal part 3 with the second needle 15 located distally of the first needle 14 with a pointed proximal end 15' of the second needle located adjacent to a distal end 14" of the first needle 14. A first end 18 of the suture 20 is coupled to the distal end 14" of the first needle 14 and a second end 18' of the suture 20 is coupled to a distal end 15" of the second needle 15. The distal part 3 also has a suture bore 17 adjacent to the proximal end 13. The suture bore 17 extends through a wall of the distal part 3 to an outside of the device 1 to allow a first suture portion 20' and a second suture portion 20" of the suture 20 to be drawn out of the needle lumen 10 toward the proximal part 2. As seen in FIG. 1, the suture bore 3 preferably extends through the wall of the distal part 3 in a direction toward the first axis 300.

The proximal part 2 includes a suture lumen 22 extending along the first axis 300 from a proximal opening 23 formed in the proximal end 5 to a distal opening 24 formed in a distal end 7 of the proximal portion 2. As shown in FIG. 3, the needle lumen 10 may preferably be circular in cross-section.

The connecting part 6 is connected between the proximal end 13 of the distal part 3 and the distal end 7 of the proximal part 2.

The suture 20 may be formed of either "resorbable" or "non-resorbable" material, as is well known in the art. The first suture portion 20' and the second suture portion 20" of the suture 20 form a loop 21 of the suture 20 (extending externally from the flexible tube 4). The first suture portion 20' extends from the first end 18 of the suture 20 around the loop 21 and the second suture portion 20" extends from the second end 18' to the loop 21. The first and second suture portions 20', 20" extend from the needle withdrawal lumen 10 through the suture bore 17 to enter and extend through the interior suture lumen 22 of the proximal part 2 and then exit the proximal part 2 through the suture opening 23. In operation, when the first suture portion 20' is extended proximally, the first needle 14 is urged proximally through the needle opening 12 and when the second suture portion 20" is extended proximally, the second needle 15 is also urged proximally through the needle opening 12.

The device 1 may preferably be used to close punctures of 9.0 French size or smaller (each French size representing 0.013" in diameter). However, punctures larger than 9.0 French size may also be closed with the device 1. The flexible tube 4 may preferably be 6.0 or 8.0 French size and each of the needles 14, 15 may preferably be constructed of stainless steel, or Nitenol™ and be between 2" and 8" in length with a diameter between 0.010" and 0.030". Of course, those skilled in the art will understand that the size of the various components of this device are limited only by the anatomy of the blood vessel into which the device is to be introduced.

A device 50 according to a second embodiment of the present invention is shown in FIG. 4. Aside from substituting an extension channel 51 extending through the proximal part 2 for the suture bore 17 and the interior suture lumen 22 (shown in FIG. 1), as described below, the construction and operation of the device 50 is substantially identical to the device 1.

Figure 4A:
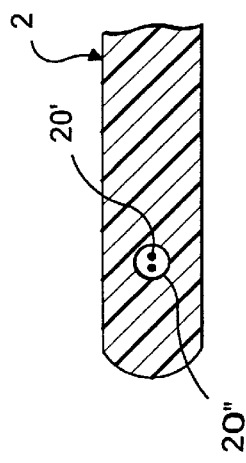
FIG. 4A shows a cross-section of the device according to the second embodiment of the present invention taken along line 4A—4A of FIG. 4.

Specifically, the extension channel 51 passes through the distal end 7 of the proximal part 2 from a first opening 51' formed on a side of the proximal part 2 opposite the second axis 301 to a second opening 51" facing the second axis 301. As shown in FIG. 4A, the extension channel 51 is shaped to allow the first and second suture portions 20', 20" to slidably extend therethrough so that the first and second suture portions 20' and 20" extend from the distal part 3 through the needle opening 12 into the second opening 51", through the extension channel 51 to exit the first opening 51' and extend along the side of the flexible tube 4 to the proximal end 5. The extension channel 51 may preferably extend substantially perpendicular to the first axis 300. Similar to the first embodiment, in order to project the first needle 14 proximally, the first suture portion 20' is pulled proximally. To project the second needle 15 proximally, the second suture portion 20" is pulled proximally.

The extension channel 51 may be situated in different locations along the proximal part 2 (e.g., closer to the proximal end 5 of the proximal part 2). In addition, the extension channel 51 may extend diagonally through the proximal part 2 with respect to the first axis 300. A second suture lumen may be provided in the proximal part 2 of the device 50 (similar to the interior suture lumen 22 illustrated in FIG. 1) connected to the extension channel 51 with the suture 20 extending from the distal part 2 through the needle opening 12 into the extension channel 51, into the suture lumen (extending through the proximal part 2) to exit the proximal part 2 of the flexible tube 4 at the proximal end 5.

Figure 5:
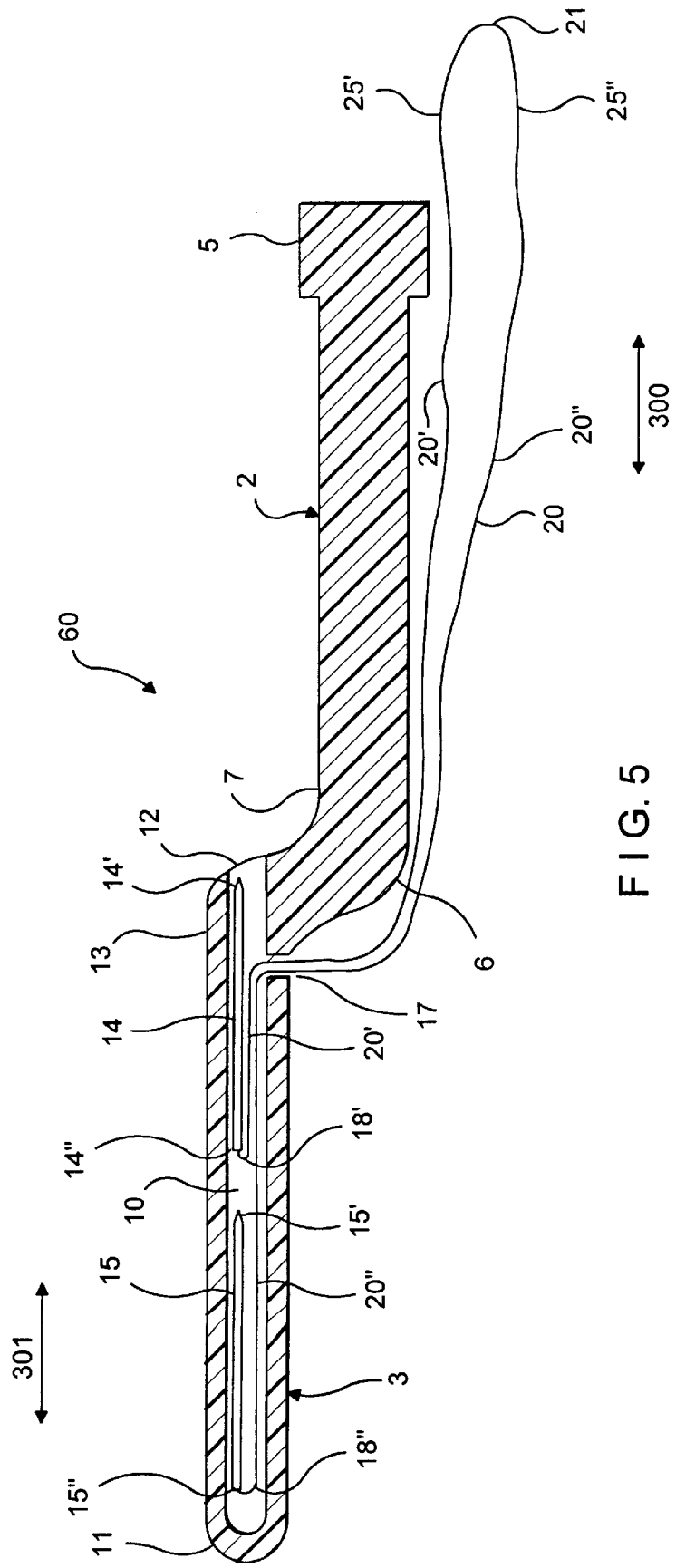
FIG. 5 shows a cross-sectional side view of a surgical suturing device according to a third embodiment of the present invention.
Figure 8:
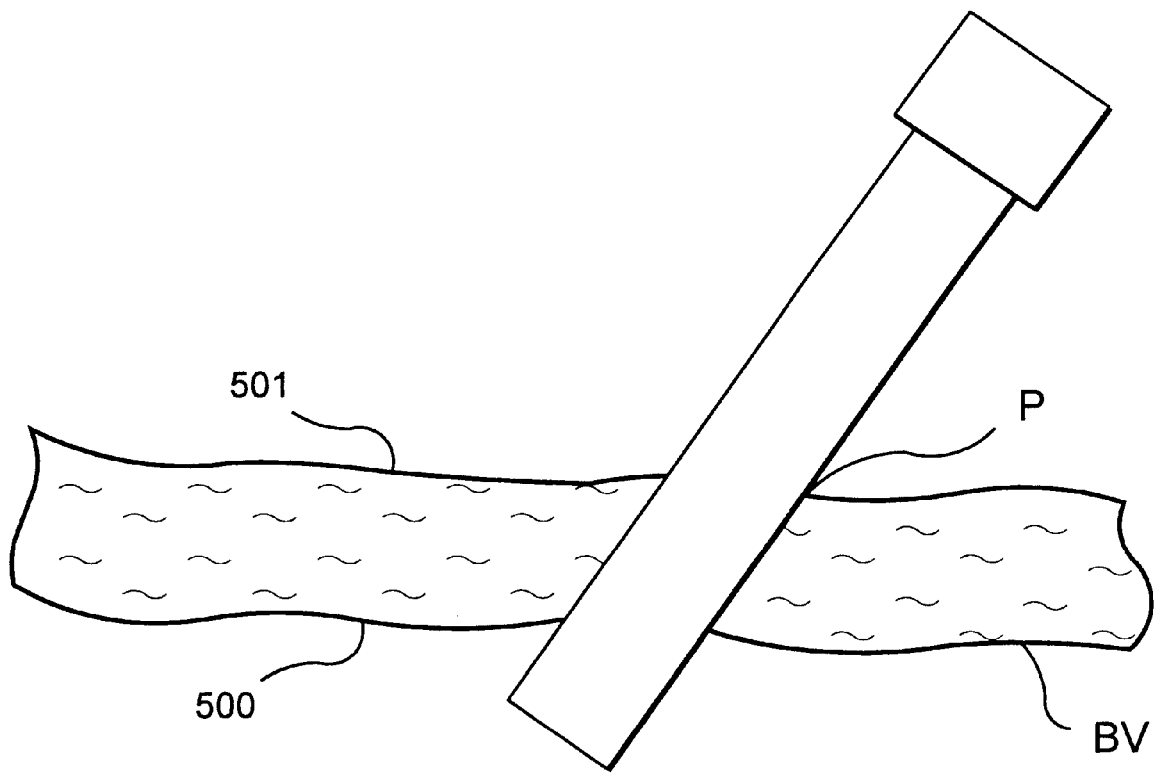
FIG. 8 shows the surgical device according to the fourth embodiment as shown in FIG. 7 penetrating the walls of the blood vessel.

A device 60 according to a third embodiment of the present invention is shown in FIG. 5. Aside from removing the interior suture lumen 22 (shown in FIG. 1) and externally extending the suture 20 on a side of the flexible tube 4 as described below, the construction and operation of the device 60 may be identical to the first embodiment (i.e., the device 1).

In particular, the first and second suture portions 20', 20" extend from the distal part 3 through the suture bore 17 to exit the distal part 3 of the flexible tube 4 and proximally extend along the side of the flexible tube 4 along the connecting part 6 to the proximal end 5.

A device 70 according to a fourth embodiment of the present invention is shown in FIG. 6, which, with a few exceptions described below, has a construction and operation substantially identical to the device 1. In particular, the fourth embodiment does not include the suture bore 17 and the interior suture lumen 22 of the device 1 and the proximal part 2 extends along a third axis 400 which is not parallel to the second axis 301. More specifically, an angle α which is preferably between 5 and 40° and which is more preferably approximately 20°. As shown in FIG. 7 (and as illustrated in FIG. 1), the first and second suture portions 20', 20" extend from the needle withdrawal lumen 10 of the distal part 3 through the needle opening 12, and extend proximally along the side of the flexible tube 4 to the proximal end 5.

An exemplary operation of the device 70 of the fourth embodiment according to the present invention (illustrated in FIGS. 6–7) is shown in FIGS. 8–14. Of course, those skilled in the art will understand that the operation of the devices 1, 50 and 60 of the first, second and third embodiments is substantially similar to the operation of the device 70 except for the path over which the suture 20 is threaded between the proximal end 5 and the needles 14 and 15.

The device 70 is inserted into a puncture P which has been made in a wall of the blood vessel during a surgical procedure and moved through the puncture P until the connecting part 6 of the flexible tube 4 is positioned within the blood vessel substantially adjacent to an inner surface 500 of the wall of the blood vessel.

Figure 9:
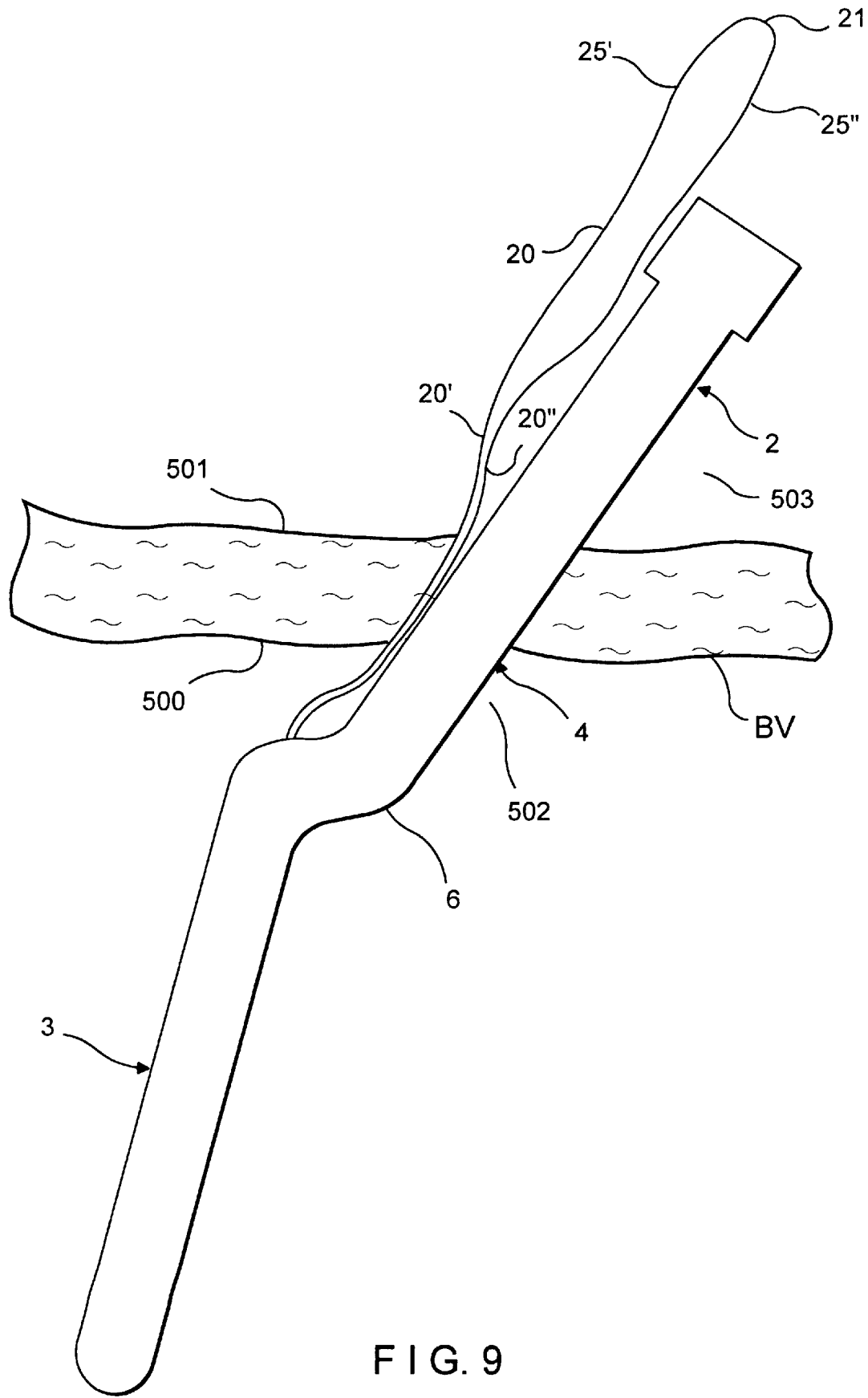
FIG. 9 shows the surgical device according to the fourth embodiment as shown in FIG. 7 in the blood vessel, with a length of suture extending through the puncture.

As the device 70 is inserted into the blood vessel, the flexible tube 4 bends so that the distal part 3 is received within, and extends in the direction of the blood vessel without straining the blood vessel. In a preferred position (as shown in FIG. 9), the distal part 3 of the flexible tube 4 is situated within the blood vessel, while only a first portion 502 of the proximal part 2 extends into the blood vessel and a second portion 503 of the proximal part 2 extends outside the blood vessel. In this orientation, the needle opening 12 is faces the inner surface 500 of the blood vessel adjacent to the puncture P and the suture 20 extends from the needle opening 12 of the distal part 3 along the side of the connecting part 6 and the proximal part 2, through the puncture P to the proximal end 5 outside the body so that the loop 21 is accessible to a user.

Figure 10:
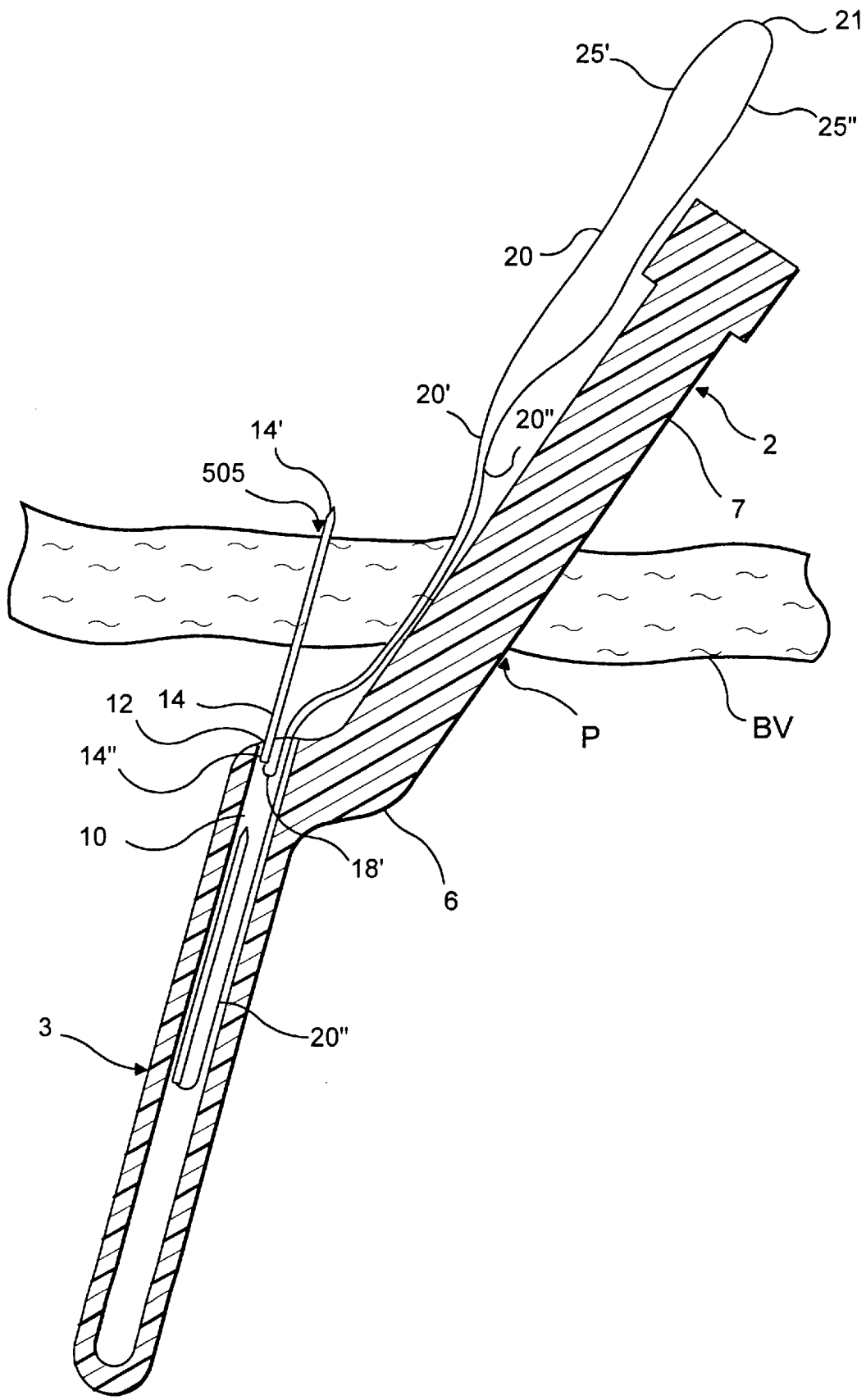
FIG. 10 shows a first needle of the device illustrated in FIG. 7 penetrating the blood vessel wall at a first position.

As shown in FIGS. 9 and 10, the user, having rotated the device 1 to a first desired angular orientation with respect to the puncture, pulls the first suture portion 20' proximally to draw the first needle 14 proximally through the needle retention lumen 10, out through the needle opening 12. Thus, the pointed end 14' of the first needle 14 is drawn through the wall of the blood vessel at a first location 505 exiting the blood vessel and the skin. The first needle 14 is drawn proximally by means of the first suture portion 20' until the pointed end 14' of the first needle 14 protrudes from the skin. The first needle 14 is then grasped by the doctor and withdrawn from the needle retention lumen 10, thereby drawing the first suture portion 20' out through the skin. In order to ensure that the first and second needles 14, 15 will extend through the skin when withdrawn from the needle withdrawal lumen 10, the first and second needles 14, 15 are preferably at least 4" in length. Of course, those skilled in the art will understand that the size of the needles employed will be limited only by the location of the puncture and the anatomy.

Figure 11:
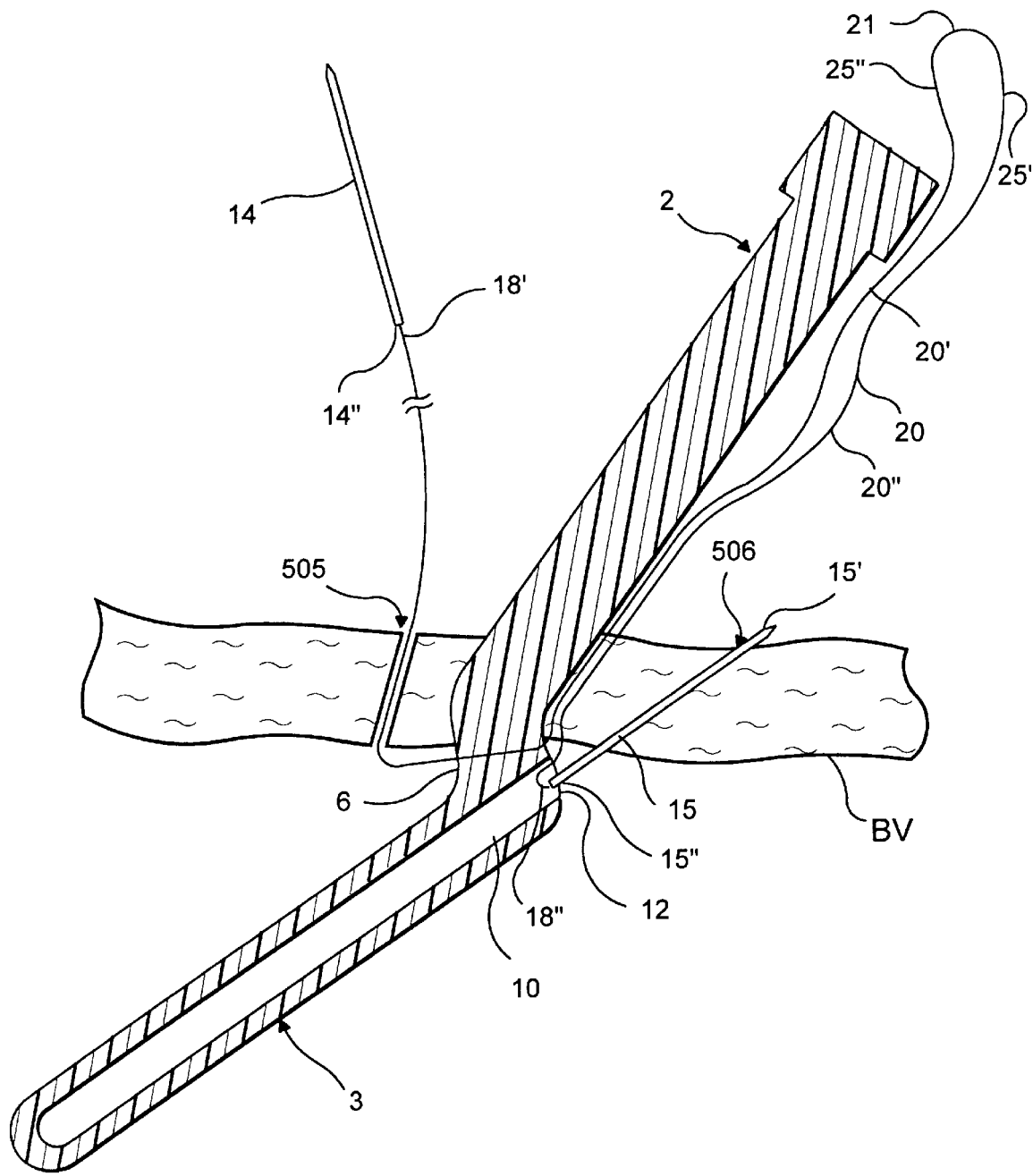
FIG. 11 shows a second needle of the device illustrated in FIG. 7 rotated within the blood vessel and penetrating the blood vessel wall at a second position.

Thereafter, the doctor rotates the device 70 within the puncture P, as shown in FIG. 11, into a second desired angular orientation in which the needle opening 12 faces a second portion 506 of the blood vessel wall. Those skilled in the art will understand that the second desired orientation may preferably be on the opposite side of the puncture P from the first position 505, so that the device 70 will be rotated approximately 180° after the first needle 14 is withdrawn from the needle retention lumen 10. When the device 70 is in the second desired orientation, the doctor pulls the second suture portion 20" proximally, thus drawing the second needle 15 proximally through the needle retention lumen 10 and out through the needle opening 12. As described above in regard to the first needle 14, the pointed end 15' of the second needle 15 is drawn through the wall of the blood vessel at the second location 506 until it protrudes from the skin. The user then grasps the second needle 15 and withdraws it, and the corresponding second suture portion 20", from the skin.

Figure 12:
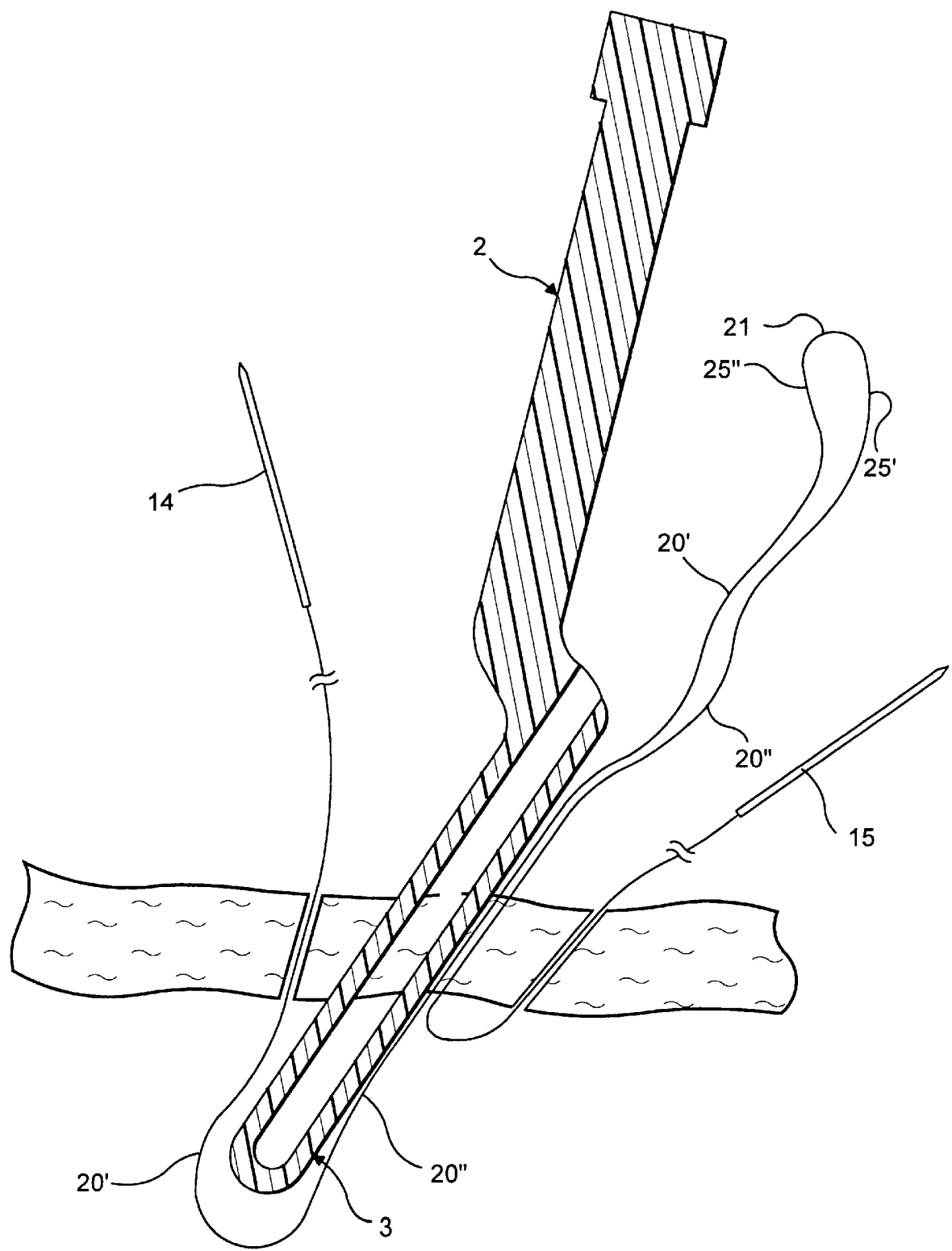
FIG. 12 shows the length of suture extending through the punctures in the walls of the blood vessel that were made at the first position and at the second position.
Figure 13:
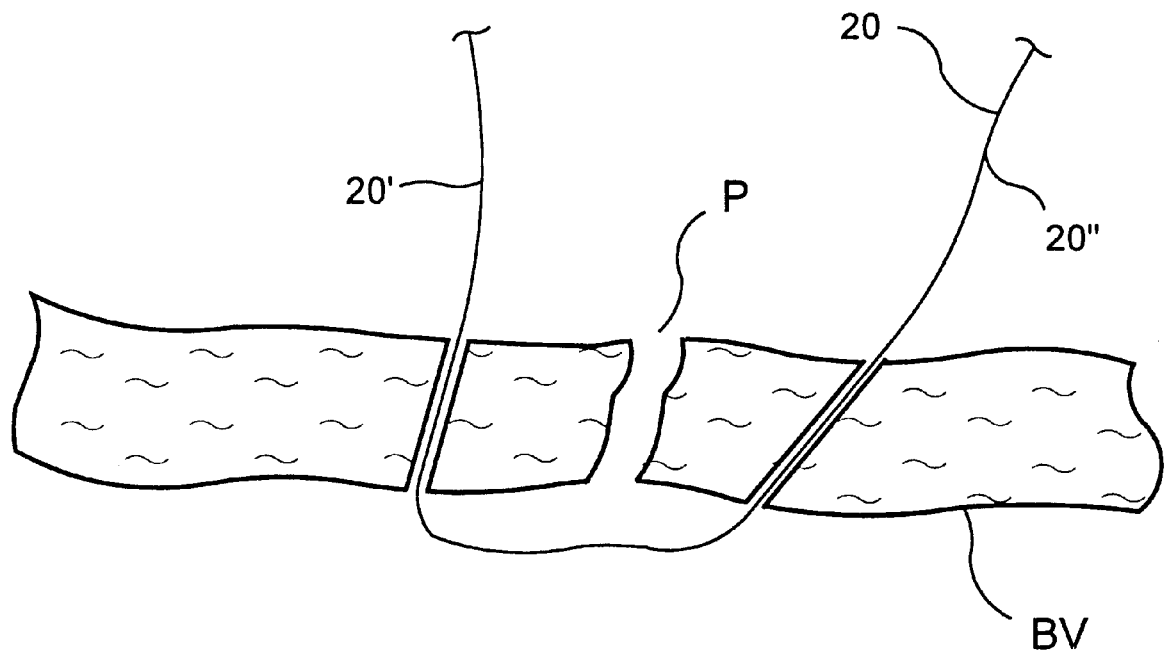
FIG. 13 shows the ends of suture being tied together.
Figure 14:
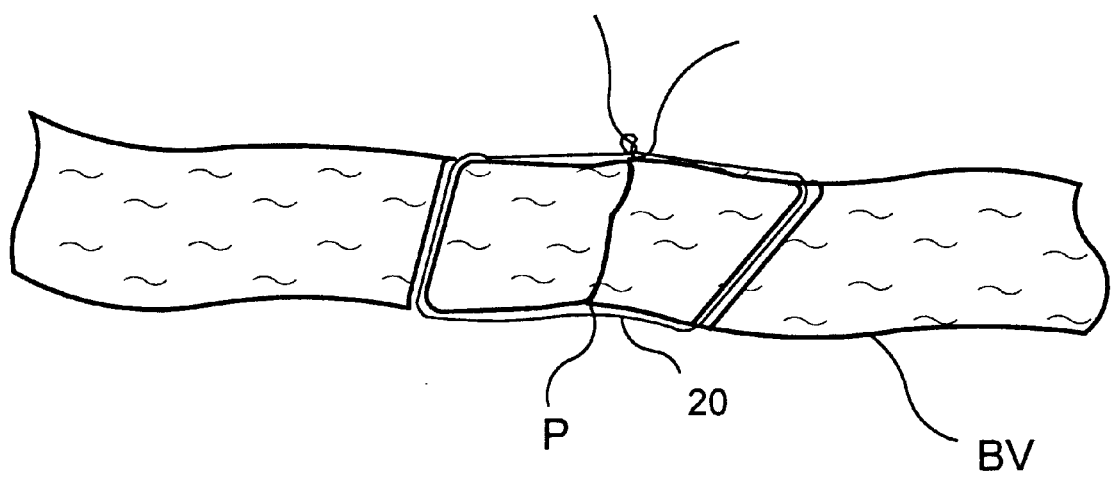
FIG. 14 shows a knot created by tying the ends of the length of suture, thus sealing the puncture in the blood vessel wall.

As shown in FIGS. 12, 13 and 14, the doctor then withdraws the device 70 from the puncture and out of the body and detaches the suture 20 from the connecting ends 14", 15" of the first and second needles 14, 15. The doctor then simultaneously pulls at the first and second ends 18', 18" of the suture 20 to close the puncture P. Finally, the first and second ends 18', 18" are tied together in a knot which is urged inward toward the blood vessel and drawn tight in order to seal the puncture. Of course, those skilled in the art will appreciate that, once the first and second ends 18', 18" of the suture 20 have been drawn through the blood vessel wall, various other methods of fastening the two ends together may be employed to seal the puncture.

A device 80 according to a fifth embodiment of the present invention, shown in FIG. 15, is substantially similar to the device 70 of the fourth embodiment (shown in FIG. 6) except that the distal part 3 of the flexible tube 4 includes two needle withdrawal lumen 88, 89 extending in a side-by-side manner parallel to the second axis 300. The first needle withdrawal lumen 88 is shaped to receive a first needle 82 and a second needle 83, with the needle 82 positioned proximally of the needle 83, along with end portions of the suture 20 which are coupled to the first needle 82 and the second needle 83. Similarly, the second needle withdrawal lumen 89 is shaped to receive a third needle 81 and a fourth needle 84 in a configuration similar to that of the first pair of needles 82, 83, along with portions of a further suture 85 coupled between the third needle 81 and the fourth needle 84. As shown in FIG. 15, each of the sutures 20 and 85 forms a suture loop 21, 87, respectively, which extends from the respective needle opening 12, 12' along the outer surface of the device 80 to the proximal end 5.

The operation of the device 80 is shown in FIGS. 17–21. As previously described above with respect to the device 70, the device 80 is inserted into the body and moved through a puncture in a blood vessel wall until the connecting part 6 of the flexible tube 4 is positioned within the blood vessel adjacent to the wall of the blood vessel. The positioning of the device 80 is substantially similar to the positioning of the device 70 described above in regard to FIGS. 10–16. The sutures 20 and 85 extend from respective first and second needle openings 12 and 12' of the distal part 3 within the blood vessel, along the side of the proximal part 2, through the puncture P, to exit the blood vessel and extend the corresponding loops 21 and 87 outside the body where they are accessible to the user.

Figure 17:
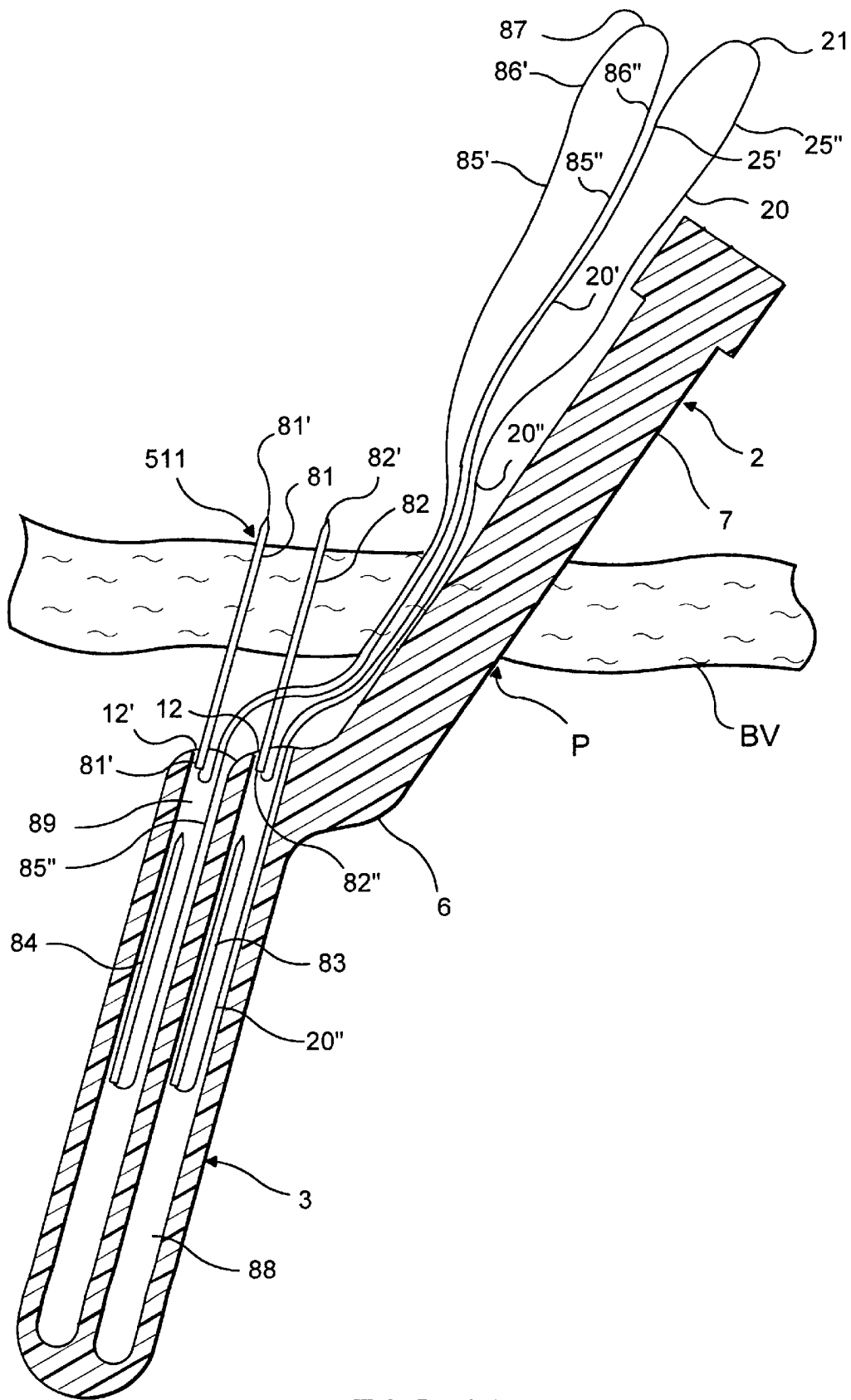
FIG. 17 shows the device according to the fifth embodiment as shown in FIG. 8 penetrating the walls of the blood vessel at two different positions.
Figure 18:
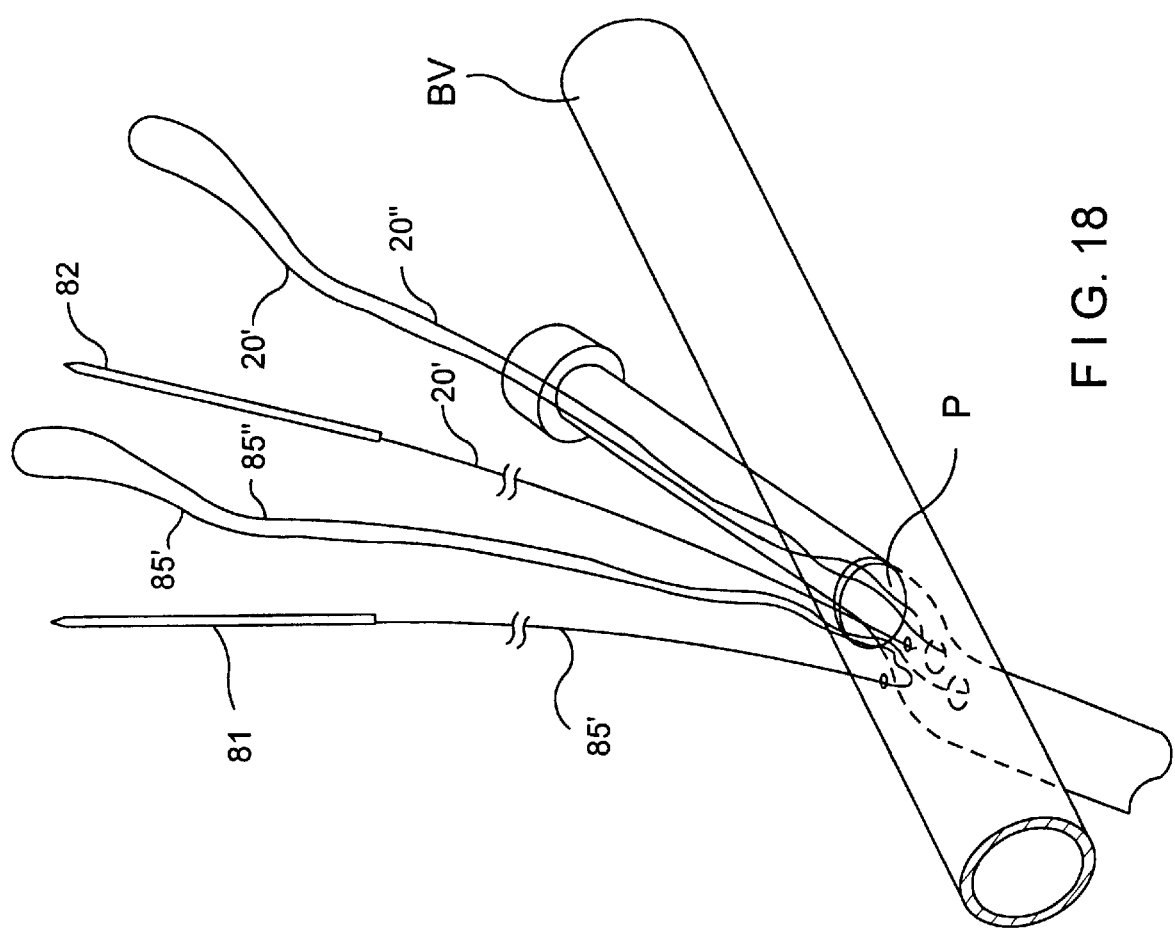
FIG. 18 shows a first pair of needles of the device illustrated in FIG. 8 penetrating the blood vessel wall at first two different positions.

As shown in FIG. 17, the doctor initially rotates the device 1 within the puncture P to a first desired angular orientation and pulls the first suture portion 20' proximally, drawing the first needle 82 proximally through the first needle retention lumen 88 and out of the first needle opening 12. The user may then pull the first suture portion 85' of the further loop 87 proximally, drawing the third needle 81 proximally through the second needle retention lumen 89 and out of the second needle opening 12'. Those skilled in the art will understand that the third needle 81 may be advanced proximally from the second needle opening 12' at the same time as the first needle 82 is drawn from the first needle opening 12 or, alternatively, may be drawn proximally either before or after the first needle is drawn proximally. Thus, the pointed end 82' of the first needle 82 is drawn through the wall of the blood vessel at a first location 510, and the pointed end 81' of the third needle is drawn through the blood vessel wall at a second location 511 and both needles 81 and 82 are advanced proximally until they protrude through the skin. The user then grasps the needles 81, 82 and completely withdraws them from the body.

Figure 19:
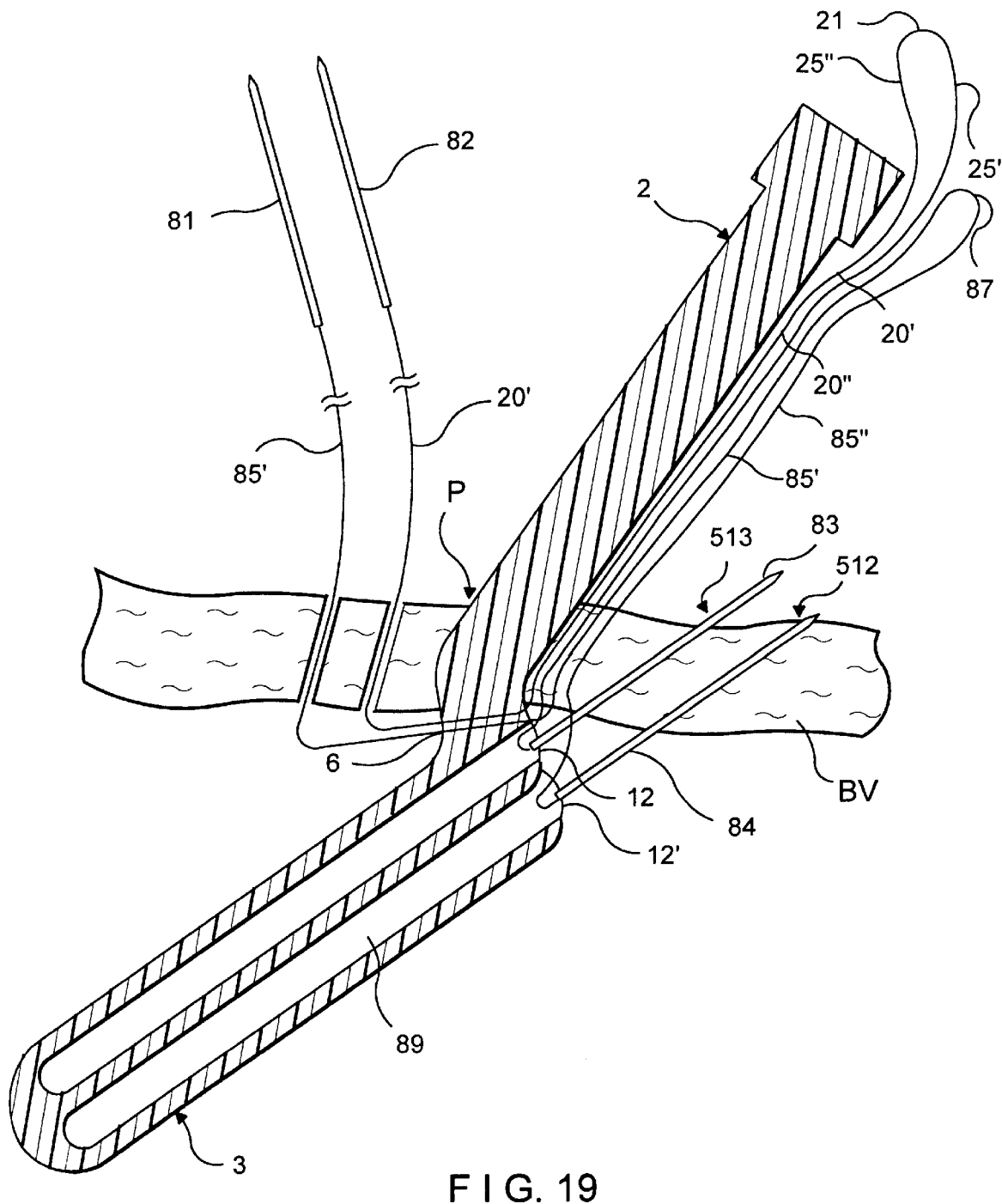
FIG. 19 shows a second pair of needles of the device illustrated in FIG. 8 rotated within the blood vessel and penetrating the blood vessel wall at second two different positions.
Figure 20:
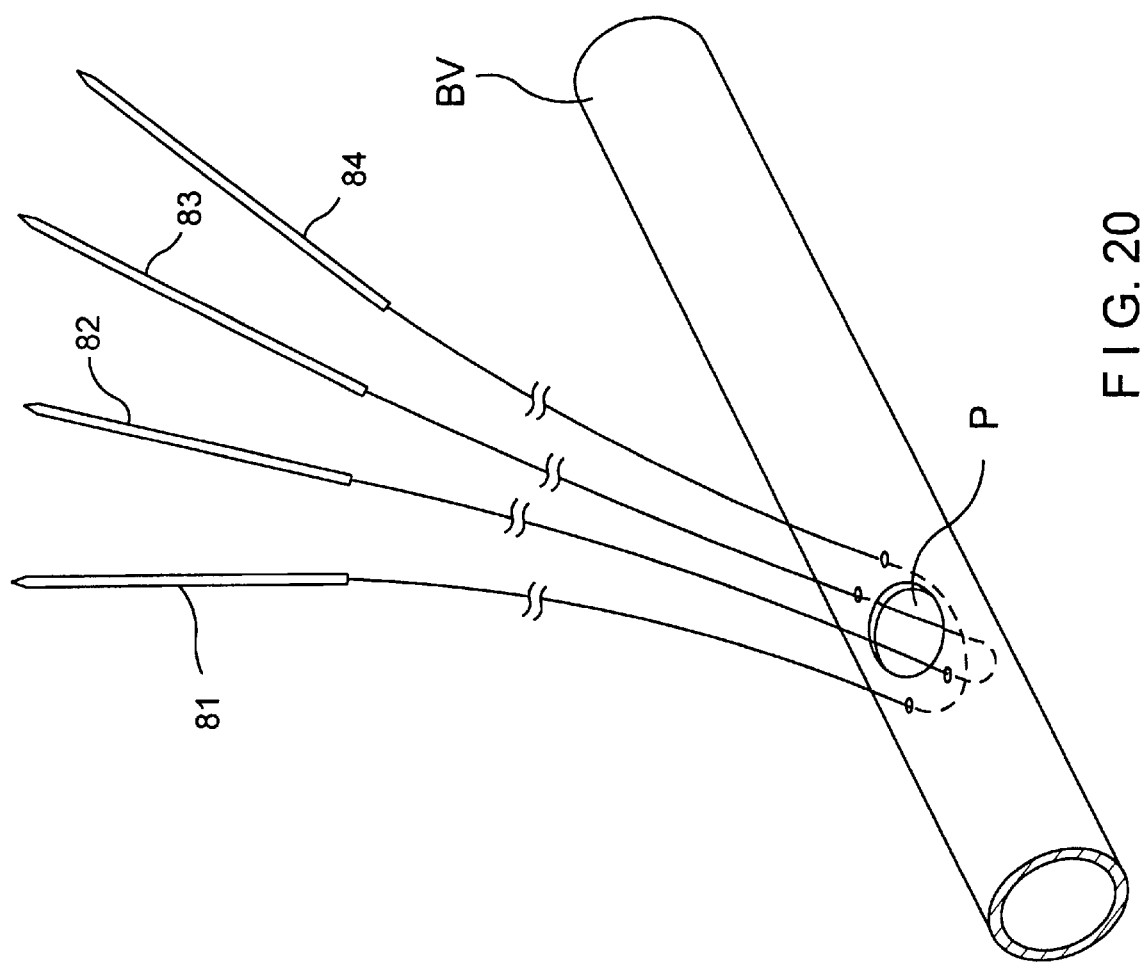
FIG. 20 shows two lengths of sutures extending through the punctures in the walls of the blood vessel that were made at the first and second different positions (i.e. four positions).
Figure 21:
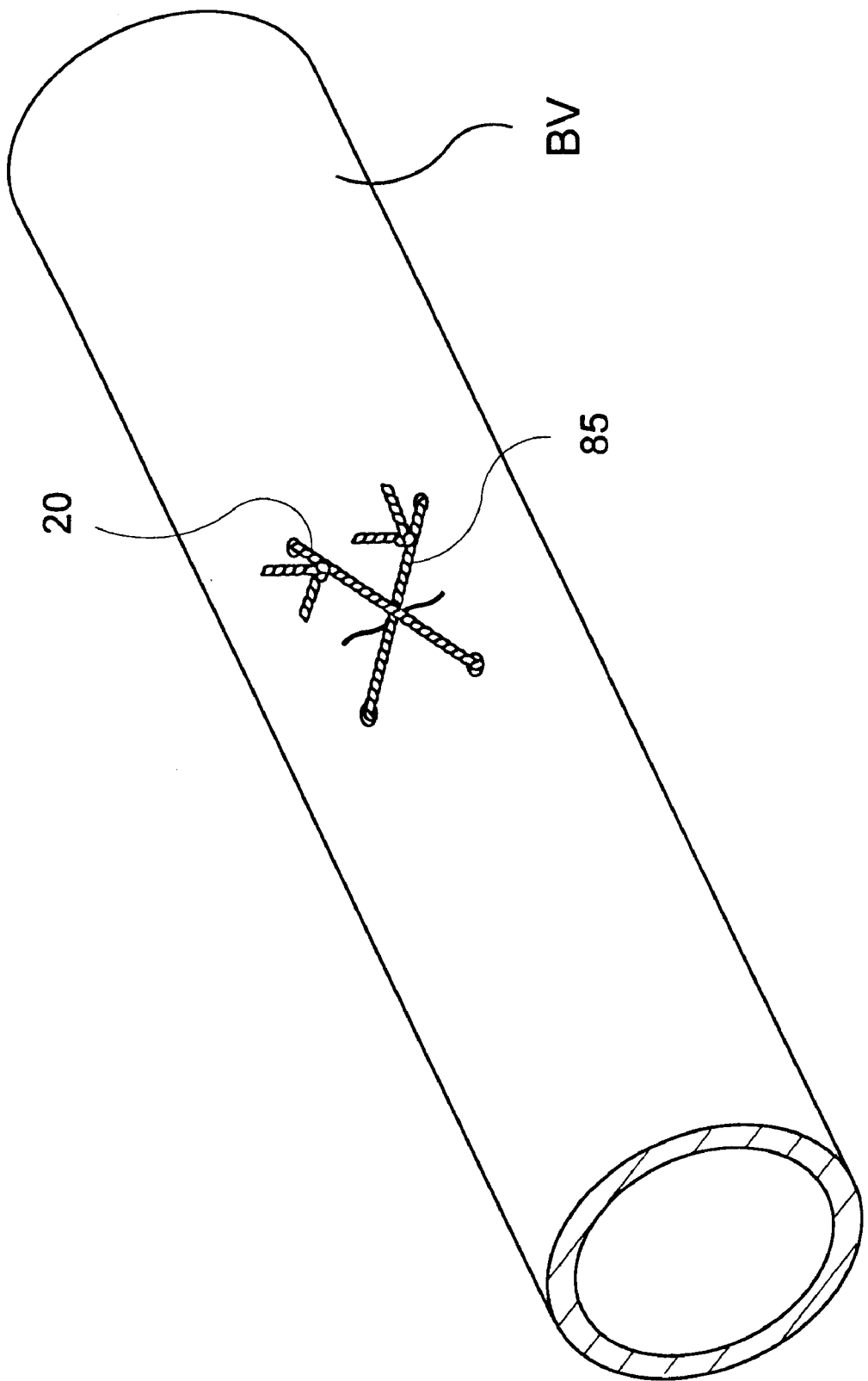
FIG. 21 shows a knot created by tying the ends of the lengths of sutures, thus sealing the puncture in the blood vessel wall.

Thereafter, the doctor rotates the device 80 within the puncture P, as shown in FIG. 19, to a second desired angular orientation with the first and second needle openings 12, 12' adjacent to portions 513 and 512, respectively, of the blood vessel wall. The user then pulls the second suture portion 20" proximally, drawing the second needle 83 proximally through the first needle retention lumen 88 and out of the first needle opening 12. The user then pulls the second suture portion 85" proximally, drawing the fourth needle 84 proximally through the second needle retention lumen 89 and out of the second needle opening 12'. As described above, the second and fourth needles 83 and 84 may be deployed simultaneously or one at a time in any order.

As described above, the pointed end 83' of the second needle 83 is drawn through the blood vessel wall at a third location 513 and the pointed end 84' of the fourth needle 84 is drawn through the blood vessel wall at a fourth location 512 and both needles 83, 84 exit the blood vessel and protrude from the skin. The first suture 20 is attached to the connecting end 83" of the second needle 83 so that the second suture portion 20" of the first suture 20 is drawn from the first needle retention lumen 88 and the second suture 85 is attached to the connecting end 85" of the second needle 84 of the second pair of needles 81, 84, so that the second suture portion 85" of the second suture 85 is drawn from the second needle retention lumen 89. The user then withdraws the device 80 from the body and detaches the sutures 20, 85 from the respective pairs of needles 82, 83 and 81, 84 (see FIG. 20). Thereafter, the doctor simultaneously pulls at the ends of the first suture 20 (and then at the ends of the second suture 85) to close the puncture P. Finally, the ends of the first and second sutures 20, 85 are tied together in one or two knots which are urged inward toward the blood vessel and drawn tight in order to seal the puncture (see FIG. 21). Of course, those skilled in the art will appreciate that, once the ends of the first and second sutures 20, 85 have been drawn through the blood vessel wall and/or skin, various other methods of fastening the four ends together may be employed.

Those skilled in the art will understand that the above described embodiments are illustrative in nature and that the many variations which will be apparent are within the scope of the invention, the scope of which is to be limited only by the claims appended hereto.

What is claimed is:

1. A device for sealing a hole in an anatomical structure within a living body comprising:
   an elongated member including a proximal portion extending along a first axis and a distal portion extending along a second axis, wherein the second axis is different from the first axis and wherein a needle retention channel extends within the distal portion to a distal portion opening formed in the proximal end of the distal portion and a central portion, wherein a proximal end of the central portion is coupled to a distal end of the proximal portion and a distal end of the central portion is coupled to a proximal end of the distal portion;
   first and second needles which, in a first configuration, are received within the needle retention channel, wherein in a second configuration, the first needle is drawn proximally out of the needle retention channel so that the entire length of the first needle is outside the elongated member while the second needle remains within the needle retention channel, and in a third configuration, the second needle is drawn proximally out of the needle retention channel so that the entire length of the second needle is outside the elongated member; and
   a loop of suture a first end of which is coupled to a distal end of the first needle and a second end of which is coupled to a distal end of the second needle, wherein, in the first configuration, the loop of suture extends through at least a portion of the needle retention channel to extend to a proximal end of the elongated member.

2. The device according to claim 1, wherein the first axis is parallel to the second axis and separated from the second axis by a predetermined distance.

3. The device according to claim 1, wherein the proximal portion includes a suture lumen extending therethrough and wherein, in the first configuration, loop of suture extends therethrough.

4. The device according to claim 3, wherein the suture lumen extends from a proximal end of the proximal portion to a distal end of the proximal portion.

5. The device according to claim 1, wherein the distal portion includes a suture bore extending from the needle retention channel to a suture bore opening formed adjacent to a proximal end of the distal portion and wherein, in the first configuration, the loop of suture extends through at least a portion of the needle retention channel and through the suture bore.

6. The device according to claim 4, wherein the distal portion includes a suture bore extending from the needle retention channel to a suture bore opening formed adjacent to a proximal end of the distal portion and wherein, in the first configuration, the loop of suture extends through at least a portion of the needle retention channel, through the suture bore and into the suture lumen.

7. The device according to claim 1, wherein the first axis is oriented at a predetermined angle with respect to second axis so that the first and second axes intersect in the distal portion.

8. The device according to claim 1, wherein the needle retention channel includes first and second needle retention channels and wherein, in the first configuration, the first and second needles are received within the first needle retention channel and third and fourth needles are received in the second needle retention channel, in the second configuration, the third needle being drawn proximally out of the second needle retention channel so that the entire length of the third needle is outside the elongated member while the fourth needle remains within the second needle retention channel and, in the third configuration, the fourth needle being drawn proximally out of the second needle retention channel so that the entire length of the fourth needle is outside the elongated member.

9. A method for sealing a hole in an anatomical structure within a living body, comprising the steps of:
   guiding into the hole an elongated member including:
      a proximal portion extending along a first axis;
      a distal portion extending along a second axis, wherein the second axis is different from the first axis and wherein a first needle retention channel extends within the distal portion to a first distal portion opening formed in the proximal end of the distal portion; and
      a central portion, wherein a proximal end of the central portion is coupled to a distal end of the proximal portion and a distal end of the central portion is coupled to a proximal end of the distal portion;
   positioning the elongated member in a first orientation within the hole so that the first distal portion opening faces a first desired location on an inner wall of the anatomical structure;
   withdrawing a first needle from the first needle retention channel by drawing proximally a first portion of a first length of suture so that a proximal end of the first needle passes through the wall of the anatomical structure wall at the first desired location, wherein a first end of the first length of suture is coupled to a distal end of the first needle;
   extracting the first needle from the body to draw the first end of the first length of suture through the anatomical structure wall to an exterior of the body;
   rotating the elongated member within the hole to a second orientation so that the first distal portion opening faces a second desired location on the inner wall of the anatomical structure;
   withdrawing a second needle from the first needle retention channel by drawing proximally a second portion of the first length of suture so that a proximal end of the second needle passes through the wall of the anatomical structure wall at the second desired location, wherein a second end of the first length of suture is coupled to a distal end of the second needle;
   extracting the second needle from the body to draw the second end of the first length of suture through the anatomical structure wall to an exterior of the body; and
   coupling the first and second ends of the first length of suture together to seal the hole.

10. The method according to claim 9, wherein the first axis extends substantially parallel to the second axis and at a predetermined distance from the second axis.

11. The method according to claim 9, wherein the distal portion further includes a second needle retention channel extending within the distal portion to a second distal portion opening, and wherein, when the elongated member is in the first orientation, the second distal portion opening faces a third desired location on the inner wall of the anatomical structure and, when the elongated member is in the second orientation, the second distal portion opening faces a fourth desired location on the inner wall of the anatomical structure, the method further comprising the steps of:

when the elongated member is in the first orientation, withdrawing a third needle from the second needle retention channel by drawing proximally a first portion of a second length of suture so that a proximal end of the third needle passes through the wall of the anatomical structure wall at the third desired location, wherein a first end of the second length of suture is coupled to a distal end of the third needle;

extracting the third needle from the body to draw the first end of the second length of suture through the anatomical structure wall to an exterior of the body;

when the elongated member is in the second orientation, withdrawing a fourth needle from the second needle retention channel by drawing proximally a second portion of the second length of suture so that a proximal end of the fourth needle passes through the wall of the anatomical structure wall at the fourth desired location, wherein a second end of the second length of suture is coupled to a distal end of the fourth needle;

extracting the fourth needle from the body to draw the second end of the second length of suture through the anatomical structure wall to an exterior of the body; and coupling the first and second ends of the second length of suture together to seal the hole.

* * * * *